(12) United States Patent
Dharmadhikari et al.

(10) Patent No.: US 11,439,600 B2
(45) Date of Patent: Sep. 13, 2022

(54) ABUSE DETERRENT ORAL SOLID DOSAGE FORM

(71) Applicant: SUN PHARMA ADVANCED RESEARCH COMPANY LIMITED, Mumbai (IN)

(72) Inventors: Nitin Dharmadhikari, Mumbai (IN); Yashoraj Zala, Mumbai (IN); Abhishek Jain, Mumbai (IN); Bramhanand Hanamannavar, Mumbai (IN); Umesh Pai, Monroe Township, NJ (US)

(73) Assignee: SUN PHARMA ADVANCED RESEARCH COMPANY LIMITED, Maharashtra (IN)

( * ) Notice: Subject to any disclaimer, the term of this patent is extended or adjusted under 35 U.S.C. 154(b) by 0 days.

(21) Appl. No.: 16/625,271

(22) PCT Filed: Jun. 22, 2018

(86) PCT No.: PCT/IN2018/050410
§ 371 (c)(1),
(2) Date: Dec. 20, 2019

(87) PCT Pub. No.: WO2018/235104
PCT Pub. Date: Dec. 27, 2018

(65) Prior Publication Data
US 2020/0222329 A1 Jul. 16, 2020

(30) Foreign Application Priority Data
Jun. 23, 2017 (IN) .............................. 201621044051

(51) Int. Cl.
*A61K 9/20* (2006.01)

(52) U.S. Cl.
CPC .......... *A61K 9/2077* (2013.01); *A61K 9/2009* (2013.01); *A61K 9/2027* (2013.01)

(58) Field of Classification Search
CPC ........................... A61K 9/2077; A61K 9/2009
See application file for complete search history.

(56) References Cited

U.S. PATENT DOCUMENTS 8,491,932 B2   7/2013 Watts et al.
9,642,811 B2 * 5/2017 Dharmadhikari .... A61K 9/2027
(Continued)

FOREIGN PATENT DOCUMENTS

JP      2016501231 A    1/2016
WO  WO-2014145195 A1   9/2014
(Continued)

OTHER PUBLICATIONS

International Application No. PCT/IN2018/050410, International Search Report and Written Opinion dated Jun. 14, 2019, 7 pages.
(Continued)

*Primary Examiner* — Timothy P Thomas
(74) *Attorney, Agent, or Firm* — Blank Rome LLP

(57) ABSTRACT

An abuse deterrent oral solid dosage form comprising:
an inner portion comprising a drug susceptible to abuse and a pH dependent polymer soluble in acidic medium
an outer portion, wherein the portion is devoid of drug susceptible to abuse and comprises an immediate release form of alkalizer and a sustained release form of alkalizer, the sustained release form of alkalizer comprising an alkalizer and a rate controlling excipient.

16 Claims, 5 Drawing Sheets

(56) References Cited

U.S. PATENT DOCUMENTS

| | | |
|---|---|---|
| 9,662,393 B2 | 5/2017 | Brzeczko et al. |
| 10,441,657 B2 | 10/2019 | Brzeczko et al. |
| 2012/0321716 A1 | 12/2012 | Vachon et al. |
| 2014/0271853 A1 | 9/2014 | Bowe et al. |
| 2015/0017240 A1 | 1/2015 | Shah et al. |
| 2015/0118303 A1 | 4/2015 | Haswani et al. |
| 2015/0272902 A1 | 10/2015 | Dharmadhikari et al. |
| 2015/0320689 A1 | 11/2015 | Dharmadhikari et al. |
| 2017/0157052 A1 | 6/2017 | Haswani et al. |

FOREIGN PATENT DOCUMENTS

| | | |
|---|---|---|
| WO | 2015145459 A1 | 10/2015 |
| WO | WO-2016023108 A1 | 2/2016 |
| WO | WO-2016094358 A1 | 6/2016 |
| WO | WO-2016120892 A1 | 8/2016 |
| WO | 2017009865 A1 | 1/2017 |

OTHER PUBLICATIONS

Aoi Ariyasu, et al.. Delay Effect of Magnesium Stearate on Tablet Dissolution in Acidic Medium, International Journal of Pharmaceutics, 2016, 511:757-764.

Extended European Search Report issued in EP18820399.6 dated Feb. 16, 2021.

* cited by examiner

ABUSE DETERRENT ORAL SOLID DOSAGE FORM

FIELD OF INVENTION

The present invention relates to abuse deterrent oral, solid dosage form that releases the drug at a desired rate for quick onset of action when a single unit or prescribed units of the dosage form are orally administered but exhibits a reduced rate of release when two or more units are administered.

BACKGROUND OF THE INVENTION

The major goal of abuse-deterrent formulations is to help reduce and prevent harm associated with the misuse and abuse of prescription medications. Currently, only a handful of prescription opioid medications have utilized these technologies in both immediate and extended-release formulations.

Pending patent application, namely, US20150272902A1, US20150320689A1 and WO2017009865A1, respectively discloses abuse deterrent oral, solid dosage forms wherein the dosage form contained an intragranular portion comprising a drug susceptible to abuse, pH dependent polymer soluble in acid and a part of alkalizer and an extragranular portion devoid of the drug susceptible to abuse and containing another part of the immediate release form of alkalizer. The present inventors have now arrived at a unique modification of the dosage form, wherein the outer portion of the oral, solid dosage form, contains alkalizer in a sustained release form comprising an alkalizer and a rate controlling excipient. When a single unit of the solid dosage form is ingested by the subject, the acidic fluids in the stomach dissolves the pH dependent polymer which is soluble in acidic pH and thus, drug is released in an unhindered manner. However, in instances where there is excess acid secretion, for e.g. in patients with hyperacidity or in patient population having acid rebound effect, there is a need for presence of excess alkalizer in the dosage form, to neutralize the acidic environment. But when excess alkalizer was incorporated, in fact the inventors faced with a problem of incomplete release of the drug susceptible to abuse from a single unit of the dosage form although release of the drug from multiple pills of the dosage form was inhibited.

The inventors surprisingly discovered that when the total alkalizer was incorporated as an immediate release form and a sustained release form, the problem of incomplete release of the drug from single unit of the dosage form was solved. The sustained release form of the alkalizer is designed such that the alkalizer is released gradually in a sustained manner over a period of about 2 hours in 0.01 N hydrochloric acid. The sustained release form of the alkalizer comprises an alkalizer and a rate controlling excipient. It was found that the sustained release form of the alkalizer when present in the outer portion of the dosage form neutralizes the acid influx over a period of few hours gradually, immediately after ingestion of the dosage form.

SUMMARY OF THE INVENTION

The present invention provides an abuse deterrent oral solid dosage form comprising:
an inner portion comprising a drug susceptible to abuse and a pH dependent polymer soluble in acidic medium, and
an outer portion, wherein the outer portion is devoid of drug susceptible to abuse and comprises an immediate release form of alkalizer and a sustained release form of alkalizer, the sustained release form of alkalizer comprising an alkalizer and a rate controlling excipient.

The present invention specifically, provides an abuse deterrent oral solid dosage form comprising:
an inner portion comprising a drug susceptible to abuse, a pH dependent polymer soluble in acidic medium and a part of the alkalizer in the immediate release form, and
an outer portion, wherein the outer portion is devoid of drug susceptible to abuse and comprises another part of immediate release form of alkalizer and a sustained release form of alkalizer, the sustained release form of alkalizer comprising an alkalizer and a rate controlling excipient.

Figure 1:
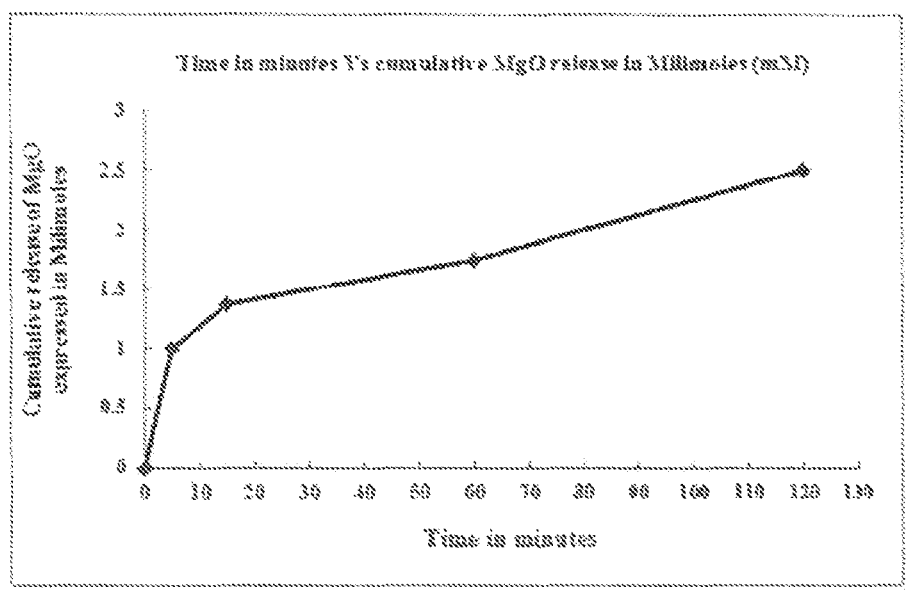
FIG. 1 illustrates the release of alkalizer from granulated mixture (matrix) of magnesium oxide as an alkalizer and ethyl cellulose as rate controlling excipient.

| Numeral Annotation | Symbol | Represents |
|---|---|---|
| 1 | Δ | Drug susceptible to abuse |
| 2 | ○ | pH dependent polymer soluble in acidic medium |
| 3 | ● | Alkalizer |
| 4 | ⊙ | Inner portion: Melt extrudate comprising of drug susceptible to abuse and pH dependent polymer soluble in acidic medium |
| 5 | — | Rate controlling excipient |
| 6 | ⊛ | Alkalizer in sustained release form having rate controlling excipient in admixture with the alkalizer |
| 7 | ⊕ | Directly compressed acetaminophen granule |
| 8 | ▢ | Abuse deterrent oral solid dosage form |

DETAILED DESCRIPTION OF THE INVENTION

The present invention may be summarized as an abuse deterrent oral solid dosage form comprising:
an inner portion comprising a drug susceptible to abuse and a pH dependent polymer soluble in acidic medium, and
an outer portion, wherein the outer portion is devoid of drug susceptible to abuse and comprises an immediate release form of alkalizer and a sustained release form of alkalizer, the sustained release form of alkalizer comprising an alkalizer and a rate controlling excipient.

According to specific embodiment of the present invention, the abuse deterrent oral solid dosage form comprises:
an inner portion comprising a drug susceptible to abuse, a pH dependent polymer soluble in acidic medium and a part of the alkalizer in the immediate release form, and
an outer portion, wherein the outer portion is devoid of drug susceptible to abuse and comprises another part of immediate release form of alkalizer and a sustained release form of alkalizer, the sustained release form of alkalizer comprising an alkalizer and a rate controlling excipient.

The phrase 'inner portion' as used herein means the portion within the dosage form in which the drug susceptible to abuse is present and is the portion in which the pH dependent polymer soluble in acidic medium is present along with the drug. The inner portion can be a single unit for example a single core or multiple units for example granules or pellets, more specifically extruded pellets and even more specifically extruded-spheronized pellets.

The phrase 'outer portion' as used herein means any portion within the dosage form other than the inner portion. The term inner portion is so named in view of it being made of excipients in close proximity and in admixture with the drug susceptible to abuse. The term outer portion is so named in view of its location outside the inner portion having the drug susceptible to abuse. As viewed from the space occupied by the drug susceptible to abuse, the inner portion is in close proximity or adjacent to the space and covering that space, and the outer portion is distanced from the drug susceptible to abuse and forms the space that is devoid of drug susceptible to abuse. Both inner portion and outer portion are within the dosage form.

The term 'an alkalizer in the sustained release form' or the 'sustained release form of the alkalizer' as described herein, includes the alkalizer whose release in the aqueous medium, has been altered due to inclusion of a release controlling substance or excipients. The term 'sustained' may be described by other terminology for e.g. controlled, delayed, modified, slow, altered and should be used as replaceable with the term 'sustained'. The sustained release form of the alkalizer may be in the form of matrix or reservoir type.

The amount of components of the present invention may be expressed herein as 'percent by weight' of the solid dosage form. Such expression of amount of the components is intended to mean that wherein when the dosage form is a tablet, percent by weight of the solid dosage form is intended to mean percentage by weight of the tablet; and when the solid dosage form is a capsule or sachet, percentage by weight of the solid dosage form as intended to mean percentage by weight of the total fill weight of the solid filled into the capsule or sachet.

In outer portion such as those detailed above, that are meant to be compressed together with or on the inner portion, means for keeping the immediate release alkalizer in the immediate release form should be adopted and excipients such as polymers that may inhibit the release are not to be directly mixed with the immediate release alkalizer portion. It will also be understood that in the outer portion there is a sustained release form of alkalizer and this form is separately fabricated with the rate controlling excipients into granules, extrudates, coated particles and mixed in the rest of the powder or granular mixture of the outer portion. Thus, the outer portion releases the immediate release form of the alkalizer immediately and releases the sustained release form of the alkalizer gradually.

In the previous inventions described in US20150272902A1, US20150320689A1 and WO2017009865A1, the alkalizer is present in the outer portion and optionally, in the inner portion of the abuse deterrent oral, solid dosage form. It was found that when a single unit of the solid dosage form is ingested by the subject, the amount of alkalizer is such that it keeps the stomach content acidic which allows the pH dependent polymer which is soluble in acidic pH to dissolve and release the drug in an unhindered manner. When multiple units of the dosage form are administered the multiple units provide an excess of alkalizer and thus the pH dependent polymer does not dissolve and the release is inhibited. However, patients have variable degree of acid secretion and can have rebound gastric acid secretion when the stomach contents are basified. The present inventors were concerned about the failure to inhibit the release when multiple units of the dosage form are administered in view of these the alkalizer becoming insufficient due to rebound of gastric acid secretion. There was thus a need for a dosage form that could completely release the drug when a single unit is administered and inhibit the release when multiple units of the dosage form are administered over a range of population that has variable acid secretion. There was a need for a dosage form which had a range of amount of alkalizer to address any risk to failure to inhibit release when multiple units of the dosage form are given due to a late acid rebound secretion in-vivo. The inventors tried higher amounts of alkalizers to address rebound of gastric acid secretion. However, when excess alkalizer was used, the inventors faced with a problem of incomplete release of the drug susceptible to abuse from a single unit of the dosage form although there was inhibition of release of the drug from multiple pills of the dosage form. The present inventors have now found a dosage form in which the alkalizer is of two forms, one an immediate release form and one a sustained release form. This modification over the previous dosage form of US20150272902A1, US20150320689A1, and WO2017009865A1 enables one to incorporate a greater amount of alkalizer to address any risk to failure to inhibit release when multiple units of the dosage form are given due to a late acid rebound secretion in-vivo, while allowing for adequate or complete release when only a single or prescribed number of units is/are administered.

The sustained release form of the alkalizer is designed such that the alkalizer is released gradually in a sustained manner over a period of about 2 hours in 0.01 N hydrochloric acid. It was found that the sustained release form of the alkalizer when present in the outer portion of the dosage form neutralizes the acid influx over a period of few hours gradually after ingestion of the dosage form. The sustained release form of alkalizer may be present as a matrix system in which alkalizer and a rate controlling excipient are in admixture. The sustained release form of alkalizer may be present in the form of coated system, also referred to reservoir system in which alkalizer is coated with a rate controlling excipient. In one embodiment, when the system is a matrix system, the sustained release form of the alkalizer releases the alkalizer in two phases, first phase with a relatively faster release over a period of 20 minutes and second phase where the release takes place slowly, the release is biphasic however overall release is herein defined as sustained release. When the system is reservoir type of system, the release of alkalizer is approximately slow, zero order release. This is also termed as sustained release herein and no difference in terminology between release from matrix type and reservoir type systems is intended, the term sustained release covers both release patterns. It is however understood that the alkalizer in the sustained release form is not all released immediately which is what distinguishes it from the alkalizer in immediate release form. The release of the alkalizer from a matrix type of system is illustrated in FIG. 1. In one specific embodiment of the matrix type of sustained release alkalizer, the alkalizer is magnesium oxide and the rate controlling excipient is ethyl cellulose, a water insoluble polymer. Depending upon the type of sustained release form i.e. either matrix or reservoir and depending upon the type of the alkalizer, the weight ratio between the alkalizer and the rate controlling excipient may vary. According to an embodiment, the release of alkalizer from sustained release form of alkalizer is at least about 25% in 5 minutes, about 35% is released in 15 minutes, about 40% in is released in 60 minutes and about 60% is released in 120 minutes in 300 ml of 0.01 N HCl with continuous stirring with magnetic stirrer. In certain preferred embodiments, 1.0 millimoles to 7 millimoles of alkalizer is released gradually in a sustained manner over a period of time. In certain embodiments, the type of sustained release form of the alkalizer depends upon the process by which it is prepared. When the rate controlling excipient is hydrophobic or water insoluble, it is dissolved in an organic solvent and is used to granulate the alkalizer. In this type, the sustained release form of alkalizer may be a matrix type or a reservoir type, in which the polymer is admixture with the alkalizer and also has as a coating layer on the alkalizer. In the processes, where the rate controlling excipient is dissolved in a solvent and spray coated on the alkalizer, reservoir type of sustained release alkalizer is obtained.

The alkalizers present in the abuse deterrent oral solid dosage form of the present invention may be water soluble or water insoluble or both. Suitable examples of the water insoluble or water soluble alkalizer, include, but are not limited to magnesium oxide, barium hydroxide, strontium hydroxide, calcium hydroxide, sodium hydroxide, potassium hydroxide, sodium carbonate, magnesium carbonate, rubidium hydroxide, cesium hydroxide, lithium hydroxide, carbonate and bicarbonate-containing compounds such as sodium bicarbonate, potassium bicarbonate and calcium carbonate; and hydroxide containing compounds such as aluminium hydroxide and magnesium hydroxide. Particular examples, include aluminium hydroxide, bismuth aluminate, bismuth carbonate, bismuth subcarbonate, bismuth subnitrate, calcium carbonate, calcium phosphate, dibasic calcium phosphate, dihydroxyaluminum aminoacetate, dihydroxyaluminum sodium carbonate, glycine, magnesium glycinate, magnesium hydroxide, magnesium oxide, potassium bicarbonate, sodium bicarbonate, sodium potassium tartrate, tribasic sodium phosphate and tricalcium phosphate and mixture thereof. The total amount of alkalizer present per unit of the oral, solid dosage form of the present invention may vary depending upon which alkalizer is present in the dosage form and the drug susceptible to abuse used. Thus, the amount of alkalizer present in the solid dosage form is the amount that provides complete release when one or prescribed number of units are ingested which is also the amount of alkalizer that is sufficient to neutralize the acid in stomach when more than prescribed number of units is ingested. The total amount of alkalizer present in the dosage form is expressed in terms of millimoles. In an embodiment, the alkalizer present is a mixture of sodium carbonate, sodium bicarbonate and magnesium oxide. The total amount of alkalizer is in the range of about 3.75 to 6 millimoles per unit abuse deterrent oral solid dosage form wherein the immediate release form of alkalizer is in the range of about 1.0 to 3.5 millimoles and the sustained release form of alkalizer is in the range of about 1 to 6 millimoles, wherein the alkalizers employed are sodium carbonate, sodium bicarbonate and magnesium oxide. However, the total amount of alkalizer may vary depending upon the type of alkalizer used. In one preferred embodiment, the total amount of alkalizer is in the range of about 3.75 to 6 millimoles per unit abuse deterrent oral solid dosage form in which the immediate release form of alkalizer is in the range of about 0.2 to 2.8 millimoles and the sustained release form of alkalizer is in the range of about 1.4 to 4.2 millimoles. In yet another embodiment, the immediate release form of alkalizer is in the range of about 0.2 to 2.8 millimoles and the sustained release form of alkalizer is in the range of about 1.4 to 6 millimoles and the total amount of alkalizer is in the range of about 3.75 to 6 millimoles per unit abuse deterrent oral solid dosage form.

The rate controlling excipient of the sustained release form of alkalizer may be polymeric or non polymeric in nature. Suitable examples, include, but are not limited to, ethyl cellulose, cellulose acetate, hydroxyethyl cellulose, hydroxypropyl methyl cellulose, methyl cellulose, carboxymethyl cellulose, hydroxyethyl methylcellulose, hydroxypropyl cellulose or the like or mixtures thereof. Preferably, the rate controlling excipient is water insoluble or hydrophobic. The hydrophobic and non-polymeric rate controlling excipients that are used preparation of sustained release form of alkalizer of the oral solid dosage form the present invention, include, but are not limited to, fatty acids; lower alcohol fatty acid ester, glycerol fatty acid esters; acetylated glycerol fatty acid esters, lactic acid derivatives of mono/diglycerides; sorbitan fatty acid esters and reaction mixtures of polyols and fatty acids, glycerides, vegetable oils, hydrogenated vegetable oils, and sterols or mixtures thereof. Some of the rate controlling excipients which are hydrophobic non-polymeric materials used in the present invention may have a melting point in the range of 40-100°

C. It is possible to use triglycerides as the rate release excipients. The triglycerides suitable for the present invention are those which solidify at ambient room temperature. Examples of suitable triglycerides include, but are not limited to, Hydrogenated castor oil, Castorwax, Hydrogenated coconut oil, Pureco 100 (Abitec), Hydrogenated cottonseed oil Dritex C (Abitec), Hydrogenated palm oil, Dritex PST (Abitec); Softisan 154 (Hüls), Hydrogenated soybean oil, Sterotex HM NF (Abitec); Dritex S (Abitec), Hydrogenated vegetable oil and so on.

The ratio of the polymeric or non polymeric material to the alkalizer that retards the release of the alkalizer from the sustained release form varies depending upon the nature of the alkalizer, whether water insoluble or water soluble and also, depends upon the nature of the polymeric or non polymeric material employed. The sustained release form of alkalizer in the outer portion is configured such that the release of alkalizer is sufficient to neutralize the inflow of the acid and the amount of the alkalizer in the immediate release form in the outer portion is sufficient to neutralize the accumulated acid in the stomach, when the abuse deterrent oral, solid dosage form is ingested in the fed state of the stomach. In one specific embodiment, the alkalizer in the sustained release form contains a homogenous mixture of alkalizer and ethyl cellulose as a rate controlling excipient or substance in the weight ratio (alkalizer:ethyl cellulose) ranging from 0.5 to 25, preferably, 1, 2, 3, 4, 5, 6, 7, 8, 9, 10 and the so on. Particularly, the alkalizer in the sustained release form is such that for example, when alkalizer is magnesium oxide, one millimole equivalent is released per minute.

In embodiments, the immediate release form of the alkalizer in the outer portion is freely released in an unhindered manner, and in such embodiments the outer portion may be a powder or granules that are physically separated from the inner portion. For example the inner portion in the form of agglomerated particles such as granules, extrudates, pellets, minitablets etc. may be filled into a capsule or sachets or containers and then the outer portion containing the alkalizer in the form of powder of granules may be then filled. According to another embodiment, one can prepare the outer portion as a freely disintegrating compression coating by means of compressing the inner portion and outer portion together with the use of known disintegrating agents, particularly superdisintegrants such as cross-linked polyvinyl pyrrolidone, cross-linked carboxymethylcellulose, sodium starch glycolate and the like; and/or with the use of wicking agents such as silicified microcrystalline cellulose. In embodiments, the granules, pellets, extrudates forming the inner portion may be simply mixed with the outer portion comprising the immediate release form and the slow release form of alkalizer and then compressed together into a tablet. Alternately the inner portion may be compressed into a core tablet and the outer portion is applied as a compression coating over the core tablet, the compression coating being formulated so as to be freely disintegrating.

The inner portion of the abuse deterrent oral, solid dosage form of the present invention comprises a 'pH dependent polymer soluble in acidic medium'. Above a critical pH, the polymers functions as a release rate controlling excipient and inhibits the release of the drug susceptible to abuse. It includes a polymer which is soluble at or below pH 5 or a polymer which is soluble at or below pH 5.5. Below the critical pH, the polymer dissolves and thus the drug release is not inhibited making the drug bioavailable when a single unit of the dosage form is administered. The term 'pH dependent polymer soluble in acidic medium' includes either a polymer which is soluble at or below pH 5 or a polymer which is soluble at or below pH 5.5.

Examples are the polymers that have group capable of accepting the hydrogen ion from an acid below the critical acidic pH and thus becoming soluble in acid environment and fall under the class of pH dependent polymers. An example of a preferred pH dependent polymer soluble in acidic medium used is a methyl methacrylate butyl methacrylate-dimethyl aminoethyl methacrylate copolymer which is a cationic copolymer synthesized from dimethyl aminoethyl methacrylate and neutral methacrylic acid esters, more particularly as is commercially available under the trade name Eudragit™ E which is soluble below about pH 5 and swellable and permeable above about pH 5. It is depicted by the following structure.

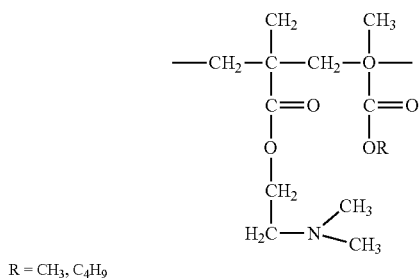

R = CH$_3$, C$_4$H$_9$

The repeating unit in the polymer has the following structure: where R represents CH$_3$ and C$_4$H$_9$ groups and the polymer has a molecular weight about 150,000. They may exist in different physical forms. The Eudragit™ E 100 product is granular, the Eudragit™ E 12.5 product is a 12.5% solution of E 100 in isopropanol and acetone, and the Eudragit EPO product is a fine powder made from E 100. Various grades of this polymer are commercially available from Evonik, Germany.

Other suitable examples of such pH dependent polymers may be found in the art. It is beneficial to use polymers which are soluble only at pH 5.5 or below, that are additionally also impermeable since this further helps control the dissolution rate. In more preferred embodiments of the present invention the reverse enteric polymer is selected from a polymer that is soluble below about pH 5 but insoluble above about pH 5.5. For example, US20050137372 disclosed similar polymers prepared by polymerizing a mixture of the hydrophobic and basic monomer or a mixture of the hydrophobic, hydrophilic and basic monomer wherein the basic monomer may be selected from the group consisting of dimethyl amino ethyl acrylate, diethyl amino ethyl ethacrylate, diethyl amino ethyl acrylate, piperidine ethyl methacrylate and 2-tert-butyl amino ethyl methacrylate. Several other polymers having basic functional groups and thus the desired pH dependent solubility behavior can be used according to the present invention. Poly(lysine) (PL), poly(ethylenimine) (PEI) and chitosan are examples of such polymers. In one embodiment, the pH dependent polymer that can be utilized in the present invention is a copolymer comprising amino and/or alkylamino and/or dialkyl amino groups such as copolymers comprising methyl methacrylate and diethylaminoethyl methacrylate such as commercially available as Kollicoat® Smartseal 30 D from BASF. The polymer has a molecular weight of about 200,000 and a glass transition temperature of 57° C. to 63° C.

The pH dependent polymer soluble in acidic medium is present in the range of 1 to 30%, more preferably in the range of 3 to 20% and most preferably in the range of 5 to 15% by weight of the of the single unit oral, solid dosage form. The pH dependent polymer soluble in acidic medium is present in the range of 10, 20, 30, 40, 50, 60, 70, 80 or 90%, more preferably in the range of 30 to 85% and most preferably in the range of 40 to 80% by weight of the inner portion. Also, in certain embodiments, the weight ratio of total alkalizer to the pH dependent polymer soluble in acidic medium in the oral solid dosage form is in the range of about 2.0 to 3.0.

According to one embodiment of the present invention, the inner portion of the abuse deterrent oral, solid dosage form contains an alkalizer. The alkalizer present in the inner portion is always present in the immediate release form and is not present in the sustained release form. The alkalizer in the inner portion is present in amounts that does not cause neutralization of the gastric acid when single or prescribed number of units of the dosage form is/are subjected to dissolution or ingested, thereby allowing complete release of the drug as the pH dependent polymer soluble in acidic medium, remains in the soluble state, and does not hinder the release of the drug. However, it causes neutralization of the gastric acid, when more than prescribed number of units of the dosage form are subjected to dissolution or ingested by making the gastric fluid pH alkaline thereby keeping the pH dependent polymer soluble in acidic medium, in the insoluble state hindering the release of the drug. The alkalizer in the immediate release form, present in the inner portion may be water soluble, water insoluble or combinations thereof. The inner portion of the abuse deterrent oral solid dosage form of the present invention is in the form of extrudes/granules/minitablets/coated particles. The extrudes/granules/minitablets/coated particles may be prepared by various processes known in the art such as hot melt extrusion, hot melt granulation, direct compression, wet granulation, dry granulation, compaction; however, melt extrusion is preferred. In one embodiment the inner portion is composed of granules comprising the drug susceptible to abuse, a pH dependent polymer soluble in acidic medium and one or more alkalizers in the immediate release form. In another embodiment, the inner portion is granules comprising the drug susceptible to abuse and a pH dependent polymer soluble in acidic medium. In another embodiment, the inner portion is compressed minitablet comprising the drug susceptible to abuse, a pH dependent polymer soluble in acidic medium and one or more alkalizers in the immediate release form. In yet another embodiment, the inner portion is a compressed minitablet comprising the drug susceptible to abuse and a pH dependent polymer soluble in acidic medium.

According to the present invention, the inner portion of the abuse deterrent oral, solid dosage form comprises a drug susceptible to abuse which includes, but is not limited to, opioids, central nervous system depressants and stimulants. The opioids are usually prescribed to treat pain. Central nervous system depressants are used to treat anxiety and sleep disorders and the stimulants are most often prescribed to treat attention deficit hyperactive disorder. Opioids act by to specific proteins called opioid receptors, which are found in the brain, spinal cord, gastrointestinal tract, and other organs in the body. When these drugs bind to their receptors, they reduce the perception of pain. Opioids can also produce drowsiness, mental confusion, nausea, constipation, and, depending upon the amount of drug taken, can depress respiration. Some people experience a euphoric response to opioid medications, since these drugs also affect the brain regions involved in reward. Those who abuse opioids may seek to intensify their experience. According to the present invention, the drug susceptible to abuse may be an opioid. The opioids are selected from the group consisting of, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tapentadol, tilidine, tramadol, pharmaceutically acceptable salts thereof, and mixtures thereof.

According to the present invention, the drug susceptible to abuse may be central nervous system (CNS) depressants. The central nervous system (CNS) depressants are selected from the group consisting of, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate, amobarbital, aprobarbotal, butabarbital, butalbital, methohexital, mephobarbital, metharbital, pentobarbital, phenobarbital, secobarbital, pharmaceutically acceptable salts thereof, and mixtures thereof. According to the present invention, the drug susceptible to abuse may be central nervous system (CNS) stimulants. The central nervous system (CNS) stimulants are selected from the group consisting of, but are not limited to, amphetamines, dextroamphetamine, methamphetamine, methylphenidate, pharmaceutically acceptable salts thereof and mixtures thereof. The drug susceptible to abuse is present in the range of 0.2 to 10% by weight of the single unit oral, solid dosage form, more preferably it is present in a range of 0.3 to 8% by weight and most preferably in the range of 0.5-6% by weight, of the single unit oral, solid dosage form.

In one specific embodiment, the pH dependent polymer soluble in acidic medium is methyl methacrylate and diethyaminoethyl methacrylate copolymer, the drug susceptible to abuse is hydrocodone bitartrate and alkalizer in the immediate release form is sodium carbonate, sodium bicarbonate, magnesium oxide and alkalizer in the sustained release form is a matrix type having magnesium oxide and ethyl cellulose. In such embodiment, when the total amount of alkalizer ranges from 3.75 millimoles to 6.0 millimoles, the weight ratio of total alkalizer and the pH dependent polymer soluble in acidic medium is between 2.0 to 3.0, sustained release form of the alkalizer present in the outer portion is in the range of 1.5 millimoles to 4.5 millimoles and the immediate release form of the alkalizer that is present in the inner and outer portion is in the range of 2.2 millimoles to 3.0 millimoles, there occurred complete release of the hydrocodone bitartrate from single unit of the dosage form when tested in vitro dissolution in 500 ml of 0.01 N HCl. In yet another such embodiment, the immediate release form of alkalizer is in the range of about 0.2 to 2.8 millimoles and the sustained release form of alkalizer is in the range of about 1.4 to 6 millimoles and the total amount of alkalizer is in the range of about 3.75 to 6 millimoles per unit abuse deterrent oral solid dosage form.

In another such embodiment, when the pH dependent polymer soluble in acidic medium is methyl methacrylate and diethyaminoethyl methacrylate copolymer, the drug susceptible to abuse is tapentadol hydrochloride and alkalizer in the immediate release form is sodium carbonate, sodium bicarbonate, magnesium oxide and alkalizer in the sustained release form is a matrix type having magnesium oxide and ethyl cellulose. In such embodiment, when the total amount of alkalizer ranges from 3.75 millimoles to 5.0 millimoles, the weight ratio of total alkalizer and the pH dependent polymer soluble in acidic medium is the range of 2.0 to 3.0, the sustained release form of the alkalizer present in the outer portion is in the range of 2.0 millimoles to 4.5 millimoles and the immediate release form of the alkalizer present in the inner and outer portion is in the range of 1.2 millimoles to 2.0 millimoles, there occurred complete release of the tapentadol hydrochloride from single unit of the dosage form when tested in vitro dissolution in 500 ml of 0.01 N HCl. In yet another such embodiment, the immediate release form of alkalizer is in the range of about 0.2 to 2.8 millimoles and the sustained release form of alkalizer is in the range of about 1.4 to 6 millimoles and the total amount of alkalizer is in the range of about 3.75 to 6 millimoles per unit abuse deterrent oral solid dosage form.

The abuse deterrent oral, solid dosage form of the present invention may be fabricated into a suitable form such as sachets, capsules or tablet by methods known in the art and using conventional excipients known in the art such as diluents or fillers, binders, disintegrants, stabilizers, glidants, lubricants, surfactants, solubilizing agents, preservatives, coloring agents and others as may be necessitated by the drug to be incorporated in the dosage form.

Figure 2:
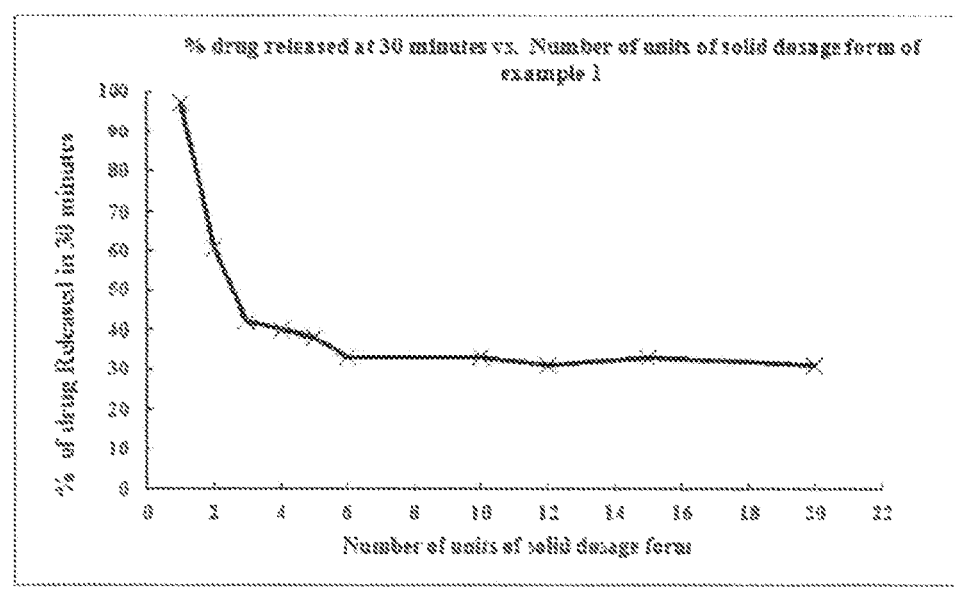
FIG. 2 is a graph of % of drug released at 30 minutes when the solid abuse deterrent oral solid dosage form of Example 1, was tested for the in vitro dissolution in 0.01 N hydrochloric acid. 1, 2, 3, 4, 5, 6, 10, 12, 15 and 20 units were tested, respectively. It can be noted that as the number of units tested increases, the percentage of the drug released at a particular time point decreases. It is to be noted, however, that the release of the drug in single unit is unaffected and complete release of drug takes place, thus, providing the drug in its therapeutically effective amount to the patient. However, the abuse deterrent oral solid dosage form of the present invention does not provide excess amount of drug, desired to be released, to the abuser, who intends to administer more than the prescribed number of units of the solid dosage form.
Figure 3:
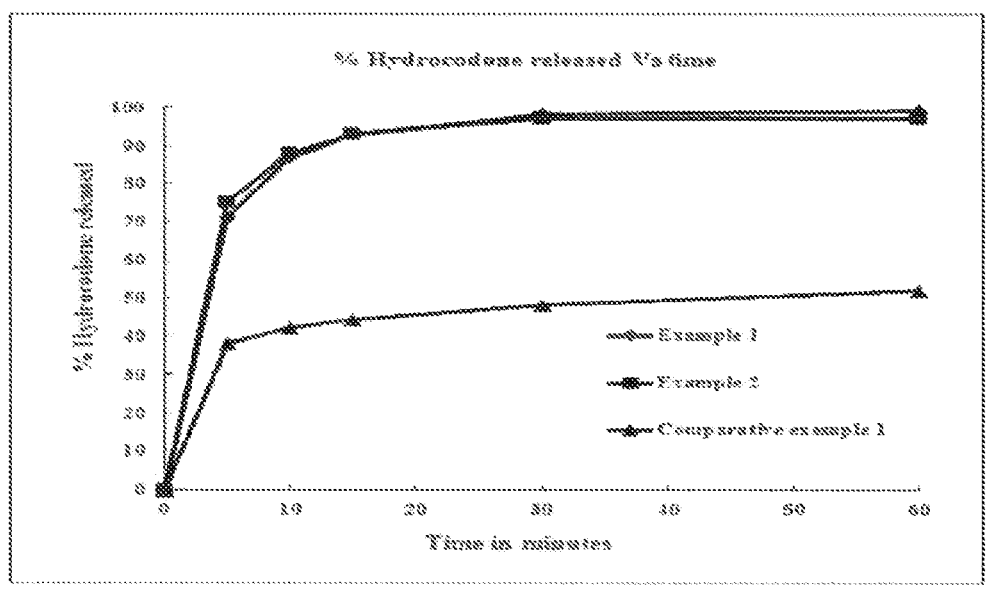
FIG. 3 is a graph of % of drug released when single tablet unit of the solid abuse deterrent oral solid dosage forms of Comparative Example 1 and Example 1 and Example 2 were tested for the in vitro dissolution in 500 ml of 0.01N hydrochloric acid. The tablet of Comparative Example 1 released only about 52% of hydrocodone in 60 minutes from single tablet whereas the dosage form of examples 1 and 2 showed complete release of hydrocodone in 60 minutes.
Figure 4:
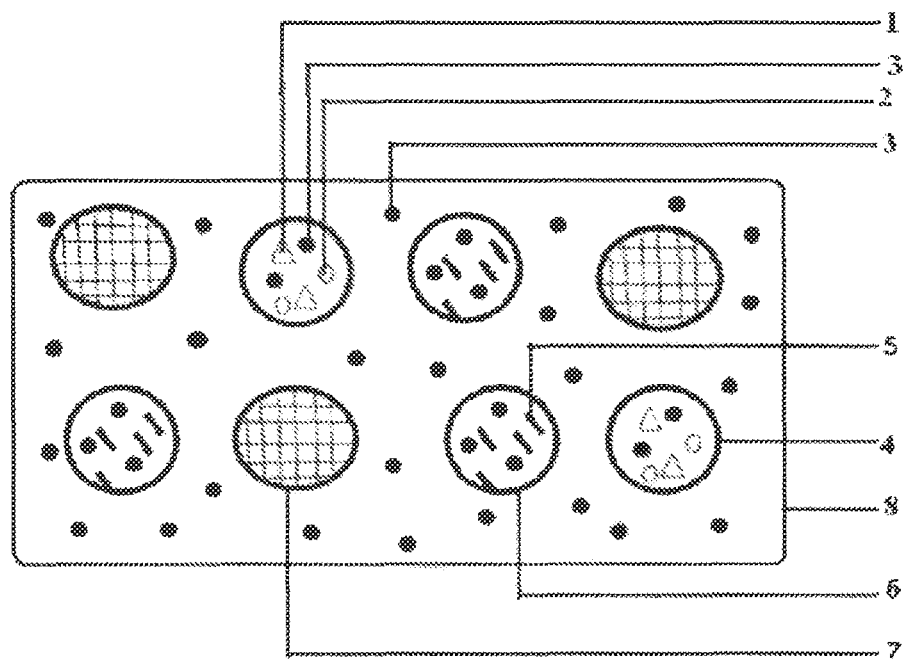
FIG. 4 is depiction of one of the embodiments of the invention wherein the abuse deterrent oral solid dosage form comprises of melt extrudates of drug susceptible to abuse (Δ), pH dependent polymer (○) and alkalizer (•) forming the inner portion. The outer portion of the oral solid dosage form comprises of sustained release granules of alkalizer with rate controlling excipient (━) and acetaminophen granules (optionally) Immediate release alkalizer is also present in the outer portion.
Figure 5:
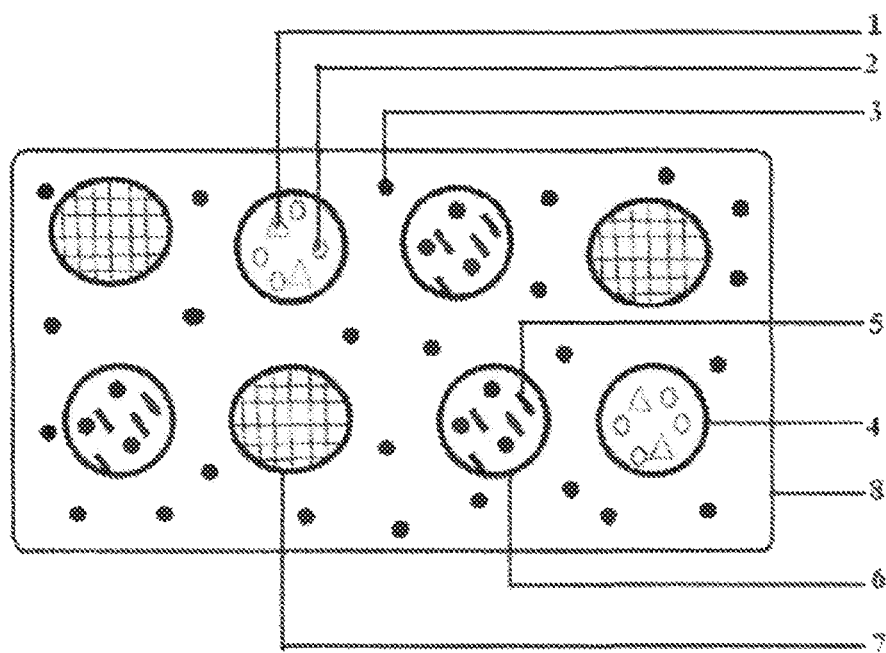
FIG. 5 is depiction of one of the embodiments of the invention wherein the abuse deterrent oral solid dosage form comprises of melt extrudates of drug susceptible to abuse (Δ) and pH dependent polymer (○) forming the inner portion. The outer portion of the oral solid dosage form comprises of sustained release granules of alkalizer with rate controlling excipient (━) and acetaminophen granules (optionally) Immediate release alkalizer is also present in the outer portion.

The total amount of alkalizer in the unit dosage form having sustained release form of alkalizer in the outer phase is the amount when present allows complete release of the drug from single or prescribed number of units and is the amount that provides inhibition of at least 30% when more than prescribed number of units are tested or ingested. For instance, in one specific example, when the dosage form contained more than 10 millimoles of alkalizer, although it provided adequate deterrence when multiple units were tested, but it hindered the release of the drug from the single unit, which is not desirable. Thus, the amount of alkalizer not only depends upon the fed or fasted condition of the stomach but also on the neutralization capacity of the alkalizer used in the dosage form. In one specific embodiment, when the total amount of alkalizer in the solid dosage form is about 5 millimoles of alkalizer per unit dosage form, it shows single unit (prescribed) when subjected to in vitro dissolution complete release of the drug takes place. When two units are tested, 61% of drug is only released, when three units are tested, just 42% of the drug is released, when four units are tested 40% of the drug is released, when five units are tested 38% of the drug is released; when six units are tested 33% of the drug is released; when ten units are tested, 33% of the drug is released; when twelve units are tested 31% of the drug is released; when fifteen units are tested, 33% of the drug is released and when twenty units are tested, 31% of the drug is only released. The data of in vitro release is depicted in FIG. 2. It may be noted that the sustained release form of alkalizer and immediate release form of alkalizer takes care of amount of hydrochloric acid present in the stomach in a fasted as well as fed state and any additional acid which may be released as an acid rebound to alkali introduced in the stomach by the dosage form of the present invention.

Thus, for example, when such number of multiple pills or a greater number are ingested by a subject, the alkalizer in the immediate release form will instantly raise the pH of the acidic environment in the stomach, whereas the alkalizer in the sustained release form will release the alkalizer in a slow manner to sustain the basic pH desirable over a period of time to achieve the abuse deterrent feature of the oral, solid dosage form. For example, when the dosage form of the present invention is configured to prevent multiple pill abuse, wherein the ingestion of the units of dosage form is more than 3 to 10, then the total amount of alkalizer present per dosage form is 1 to 3 units, with the assumption that less than 1.0 units of alkalizer are present in single unit, and therefore, when one or prescribed number of units are ingested, the alkalizer is present in amount that is insufficient to increase the pH of the stomach, leaving the pH dependent polymer soluble in acid, in the soluble form, thereby causing complete release of the drug from the single unit.

While the present invention is disclosed generally above, additional aspects are further discussed and illustrated with reference to the examples below. However, the examples are presented merely to illustrate the invention and should not be considered as limitations thereto.

Comparative Example 1

The tablet composition of Comparative Example 1 represents a composition with alkalizer only in the immediate release form and devoid of any sustained release form of alkalizer. The alkalizers namely magnesium oxide, sodium carbonate and sodium bicarbonate were present in amount of about 4.3 millimoles per tablet.

TABLE 1

Composition of Comparative Example 1

| Category of ingredients | Ingredients | Comparative Example 1 Amount in mg (millimoles) |
|---|---|---|
| Inner portion | | |
| Drug | Model candidate drug susceptible to abuse-I (Hydrocodone bitartrate) | 10 |
| pH dependent polymer soluble in acidic medium | Methyl Methacrylate & Diethylaminoethyl Methacrylate Copolymer | 100 |
| Excipient | Polyvinyl alcohol | 12.5 |
| Alkalizer in immediate release form | Magnesium Oxide | 5 (0.124 millimoles) |
| | Sodium Carbonate | 10.8 (0.102 millimoles) |

TABLE 1-continued

Composition of Comparative Example 1

| Category of ingredients | Ingredients | Comparative Example 1 Amount in mg (millimoles) |
|---|---|---|
| Excipient | Tartaric Acid | 3 |
|  | Butylated hydroxyanisole | 0.165 |
| Outer portion |  |  |
| Other drug not susceptible to abuse | Acetaminophen granule* in the form of directly compressed granules | 361.125 |
| Alkalizer In Immediate Release | Sodium Bicarbonate | 85 (1.01 millimoles) |
|  | Sodium Carbonate | 25 (0.24 millimoles) |
|  | Magnesium Oxide | 115 (2.85 millimoles) |
| Excipients | Silicified Microcrystalline cellulose | 143.11 |
|  | Crospovidone | 90 |
|  | Colloidal silicon dioxide | 10 |
|  | Talc | 7 |
|  | Magnesium Stearate | 7 |

Procedure:

A: Preparation of the Inner Portion Comprising Granules/Extrudates of Drug Susceptible to Abuse and pH Dependent Polymer Step 1: Ingredients of inner portion namely hydrocodone bitartrate, methyl methacrylate and diethyaminoethyl methacrylate copolymer (Kollicoat Smartseal® 100 P), magnesium oxide, sodium carbonate, polyvinyl alcohol, tartaric acid, butylated hydroxyl anisole were sifted separately through a suitable sieve.

Step 2: Butylated hydroxyl anisole was dissolved in ethyl alcohol and was used to granulate hydrocodone bitartrate, polyvinyl alcohol and tartaric acid.

Step 3: The granules of step 2 were mixed with specified amounts of methyl methacrylate and diethyaminoethyl methacrylate copolymer (Kollicoat Smartseal® 100 P), magnesium oxide and sodium carbonate in a blender.

Step 4: The blended mixture of step 3 was charged in hot melt extruder. The extrudates were milled and sieved through suitable sieve.

B: Preparation of the Outer Portion: The outer portion included directly compressible acetaminophen granules which are available under the brand name Compresso PAP® 90CPF** composition of which is given below.

TABLE 2

Details of directly compressed acetaminophen granules*

| Ingredients | Amount (mg) |
|---|---|
| Acetaminophen, USP | 325.01 |
| Pregelatinized Starch, NF | 25.64 |
| Povidone, USP, PVP K-30 | 5.06 |
| Crospovidone, NF | 3.61 |
| Stearic Acid, NF | 1.81 |

**The directly compressed acetaminophen granules contained the following ingredients:
**Compresso PAP ® 90CPF represents directly compressed Acetaminophen granules made by granulating with conventional tablet excipients and contains 90% by weight of Acetaminophen The outer portion further included ingredients such as immediate release form of alkalizer, superdidintegrants, wicking agents, lubricants etc.

C: Mixing the Extrudates of Inner Portion with the Ingredients of the Outer Portion and Converting it into Tablets:

All the ingredients i.e. the hot melt extrudates of the drug susceptible to abuse of the inner portion as prepared in A; specified amounts of the ingredients of the outer portion i.e. Acetaminophen granules DC 90% e.g. Compresso PAP® 90CPF**; sodium carbonate, sodium bicarbonate, silicified microcrystalline cellulose, crospovidone, colloidal silicon dioxide were dry mixed after sifting in a suitable blender. The blended dry mix was further lubricated with magnesium stearate and talc and compressed into tablets.

Example 1-2

The tablet composition of Example 1 represents a composition with alkalizers present in both immediate release form and sustained release form. The total amount of alkalizers namely magnesium oxide, sodium carbonate and sodium bicarbonate was 4.3 millimoles per tablet.

TABLE 3

Composition details of Example 1-2

| Category of ingredients | Ingredients | Example 1 Amount in mg (millimoles) | Example 2 Amount in mg (millimoles) |
|---|---|---|---|
| Inner portion |  |  |  |
| Drug | Model candidate drug susceptible to abuse- (Hydrocodone Bitartrate) | 10 | 10 |

TABLE 3-continued

Composition details of Example 1-2

| Category of ingredients | Ingredients | Example 1 Amount in mg (millimoles) | Example 2 Amount in mg (millimoles) |
|---|---|---|---|
| pH dependent polymer soluble in acidic medium | Methyl Methacrylate & Diethylaminoethyl Methacrylate Copolymer | 100 | 100 |
| Excipient | Polyvinyl alcohol | 12.5 | 12.5 |
| Alkalizer in immediate release form | Magnesium Oxide | 5 (0.124 millimoles) | 5 (0.124 millimoles) |
| | Sodium Carbonate | 10.8 (0.102 millimoles) | 10.8 (0.102 millimoles) |
| Excipient | Tartaric Acid | 3 | 3 |
| | Butylated hydroxyanisole | 0.165 | 0.165 |
| Outer portion | | | |
| Other drug not susceptible to abuse | Acetaminophen granule* in the form of directly compressed granules | 361.125 | 361.125 |
| Alkalizer In Immediate Release And Sustained Release Form | Sodium Bicarbonate immediate release form | 85 (1.01 millimoles) | 85 (1.01 millimoles) |
| | Sodium Carbonate immediate release form | 25 (0.24 millimoles) | 0 millimoles |
| | Magnesium Oxide immediate release form | 25 (0.62 millimoles) | 0 millimoles |
| | magnesium oxide in Sustained release ** | Magnesium oxide | 115.3** 90 (2.23 millimoles) | 160.139** 125 (3.1 millimoles) |
| | | Ethyl cellulose | 21.6 | 30 |
| | | Silicon Dioxide | 3.7 | 5 |
| Excipient | Silicified Microcrystalline cellulose | 143.11 | 143.11 |
| | Crospovidone | 90 | 90 |
| | Colloidal silicon dioxide | 10 | 10 |
| | Talc | 7 | 7 |
| | Magnesium Stearate | 7 | 7 |

Procedure:

A: Preparation of the Inner Portion Comprising Extrudates of Drug Susceptible to Abuse and pH Dependent Polymer Soluble in Acidic Medium:

Step 1: Ingredients of inner portion namely hydrocodone bitartrate, methyl methacrylate and diethyaminoethyl methacrylate copolymer (Kollicoat Smartseal® 100 P), magnesium oxide, sodium carbonate, polyvinyl alcohol, tartaric acid, butylated hydroxyl anisole were sifted separately through a suitable sieve.

Step 2: Butylated hydroxyl anisole was dissolved in ethyl alcohol and was used to granulate hydrocodone bitartrate, polyvinyl alcohol and tartaric acid.

Step 3: The granules of step 2 were mixed with specified amounts of methyl methacrylate and diethyaminoethyl methacrylate copolymer (Kollicoat Smartseal® 100 P), magnesium oxide and sodium carbonate in a blender.

Step 4: The blended mixture of step 3 was charged in hot melt extruder. The extrudates were milled and sieved through suitable sieve.

B: Preparation of Sustained Release Form of Alkalizer Present in the Outer Portion:

The composition of sustained release form of alkalizer is tabulated below.

TABLE 4

Composition of sustained release form of alkalizer magnesium oxide**

| Ingredients | Amount in mg |
|---|---|
| Magnesium oxide | 90.000 |
| Ethyl cellulose | 21.600 |
| Silicon Dioxide | 3.700 |

The preparation of the sustained release form of alkalizer involved the following steps:

Step 1: Specified amount of magnesium oxide and silicon dioxide were sifted through suitable sieve.

Step 2: Ethyl cellulose was dissolved in ethanol.

Step 3: The lubricated magnesium oxide of Step 1 was transferred to a fluid bed processor with a top spray assembly and was granulated with a solution of ethyl cellulose in ethanol using suitable granulation parameters.

Step 4: The granules of step 3 were sifted through suitable sieve.

C: Mixing the Extrudates of Inner Portion with the Ingredients of the Outer Portion and Converting it into Tablets:

All the ingredients i.e. the hot melt extrudates of the drug susceptible to abuse of the inner portion as prepared in A; the ingredients of the outer portion i.e. Acetaminophen granules DC 90% e.g. Compresso PAP® 90CPF; granules of magnesium oxide and ethyl cellulose as prepared in B; sodium carbonate, sodium bicarbonate and magnesium oxide; silicified microcrystalline cellulose, crospovidone, colloidal silicon dioxide were dry mixed after sifting in a suitable blender. The blended dry mix was further lubricated with magnesium stearate and talc and compressed into tablets. The compressed tablets were further coated with hydroxypropyl methylcellulose. The composition of Acetaminophen granules DC 90%—Compresso PAP® 90CPF is given below.

TABLE 5

Details of directly compressed acetaminophen granules

| Ingredients | Amount in mg |
|---|---|
| Acetaminophen, USP | 325.01 |
| Pregelatinized Starch, NF | 25.64 |
| Povidone, USP, PVP K-30 | 5.06 |
| Crospovidone, NF | 3.61 |
| Stearic Acid, NF | 1.81 |

**The directly compressed acetaminophen granules contained the following ingredients:
**Compresso PAP® 90CPF represents directly compressed Acetaminophen granules made by granulating with conventional tablet excipients and contains 90% by weight of Acetaminophen Example 3

Effect of Sustained Release Form of Alkalizer on Release of Drug From Single Unit Dosage Form The tablet of Comparative Example 1, Example 1 and Example 2 all included 4.3 millimoles of alkalizer which are magnesium oxide, sodium carbonate and sodium bicarbonate. The tablets prepared according to these examples were subjected to in vitro dissolution in 500 ml of 0.01 N HCl using USP II (Paddle) apparatus at 50 rotations per minute. Table 6 provides the distribution of millimoles of alkalizer present in sustained release form and immediate release form followed by in vitro the release of hydrocodone from a single tablet.

TABLE 6

Effect of sustained release form of alkalizer on release of drug from single unit dosage form

| Location in dosage form | Alkalizer in millimoles | Comparative Example 1 | Example 1 | Example 2 |
|---|---|---|---|---|
| Outer portion | Sustained release alkalizer | — | 2.2 | 3.1 |

TABLE 6-continued

Effect of sustained release form of alkalizer on release of drug from single unit dosage form

| | | | | |
|---|---|---|---|---|
| | Immediate release alkalizer | 4.1 | 1.9 | 1 |
| Inner portion | Immediate release alkalizer | 0.2 | 0.2 | 0.2 |

In Vitro release

| Time in minutes | % Hydrocodone released | | |
|---|---|---|---|
| 5 | 38 | 71 | 75 |
| 10 | 42 | 87 | 88 |
| 15 | 44 | 93 | 93 |
| 30 | 48 | 98 | 97 |
| 60 | 52 | 99 | 97 |

From the above in vitro dissolution results, it is apparent that when the tablets of comparative example 1 included only immediate release form of alkalizer and did not have sustained release form of alkalizer, the release of the drug was incomplete (only 52% was released at the end of 60 minutes).

Tablet of Example 1 and Example 2 had same amount of total alkalizer (i e 4.3 millimoles) but the total alkalizer was divided in varying amount of sustained release form of alkalizer and immediate release form of alkalizer. The in vitro dissolution data showed complete of hydrocodone in 60 minutes. It can be concluded that in order to achieve complete release of hydrocodone from a single tablet, the amount of sustained release alkalizer and immediate release plays an important role. In these examples, the release is complete when the total amount of alkalizer which is sum of amount sustained release form of alkalizer and immediate release form of alkalizer is in the range of 4.3 millimoles.

Comparative Example 2

The tablet composition of Comparative Example 2 represents compositions with alkalizer only in the immediate release form and devoid of sustained release form of alkalizers. The total amount of alkalizer namely magnesium oxide, sodium carbonate and sodium bicarbonate in Comparative Example 2 was in amount of about 4 millimoles per tablet. The composition of the Comparative Example 2 is tabulated below.

TABLE 7

Composition details of Comparative Example 2

| Category of ingredients | Ingredients | Comparative Example 2 Amount in mg (millimoles) |
|---|---|---|
| Inner portion | | |
| Drug | Model candidate drug susceptible to abuse - (Tapentadol Hydrochloride | 11.6 |
| pH dependent polymer soluble in acidic medium | Methyl Methacrylate & Diethylaminoethyl Methacrylate Copolymer | 100 |
| Excipient | Polyvinyl alcohol | 12.5 |
| Alkalizer in immediate release form | Magnesium Oxide | 5 (0.124 millimoles) |
| | Sodium Carbonate | 10.8 (0.102 millimoles) |
| Excipient | Tartaric Acid | 3 |
| | Butylated hydroxyanisole | 0.165 |

TABLE 7-continued

Composition details of Comparative Example 2

| Category of ingredients | Ingredients | Comparative Example 2 Amount in mg (millimoles) |
|---|---|---|
| Outer portion | | |
| Other drug not susceptible to abuse | Acetaminophen granule* in the form of directly compressed granules | 361.125 |
| Alkalizer In Immediate Release | Sodium Bicarbonate | 85 (1.01 millimoles) |
| | Sodium Carbonate | 25 (0.24 millimoles) |
| | Magnesium Oxide | 101.68 (2.52 millimoles) |
| Excipient | Silicified Microcrystalline cellulose | 132.875 |
| | Crospovidone | 90 |
| | Colloidal silicon dioxide | 10 |
| | Talc | 7 |
| | Magnesium Stearate | 7 |

Tablets of comparative examples 2 was prepared as per the procedure described in Comparative Example 1 but the model candidate drug susceptible to abuse was tapentadol hydrochloride, instead of hydrocodone bitartrate.

Example 4

The tablet composition of Example 4 represents compositions with alkalizer in both immediate release form and sustained release form. The total amount of alkalizers present in tablet composition of Example 4 was in amount of about 4 millimoles per tablet.

TABLE 8

Composition details of Example 4

| Category of ingredients | Ingredients | Example 4 Amount in mg (millimoles) | |
|---|---|---|---|
| Inner portion | | | |
| Drug | Model candidate drug susceptible to abuse (Tapentadol Hydrochloride) | 11.6 | |
| pH dependent polymer soluble in acidic medium | Methyl Methacrylate & Diethylaminoethyl Methacrylate Copolymer | 100 | |
| Excipient | Polyvinyl alcohol | 12.5 | |
| Alkalizer in immediate release form | Magnesium Oxide | 5 (0.124 millimoles) | |
| | Sodium Carbonate | 10.8 (0.102 millimoles) | |
| Excipient | Tartaric Acid | 3 | |
| | Butylated hydroxyanisole | 0.165 | |
| Outer portion | | | |
| Other drug not susceptible to abuse | Acetaminophen granule* in the form of directly compressed granules | 361.125 | |
| Alkalizer In Immediate Release and Sustained Release Form | Sodium Bicarbonate (immediate release form) | 85 (1.01 millimoles) | |
| | Sodium Carbonate (immediate release form) | 25 (0.24 millimoles) | |
| | Magnesium Oxide in Sustained Release ** | Magnesium Oxide | 132.00** | 101.68 (2.5 millimoles) |
| | | Ethyl cellulose | 30.32 |
| Excipients | Silicified Microcrystalline cellulose | 132.875 | |
| | Crospovidone | 90 | |
| | Colloidal silicon dioxide | 10 | |
| | Talc | 7 | |
| | Magnesium Stearate | 7 | |

The tablet composition of example 4 was prepared as per the procedure described in example 1 but the model candidate drug susceptible to abuse was tapentadol hydrochloride, instead of hydrocodone bitartrate.

Example 5

Effect of Sustained Release Form of Alkalizer on Release of Drug From Single Unit Dosage Form The tablet of Comparative Example 2 and Example 4 both included about 4 millimoles of alkalizer which are magnesium oxide, sodium carbonate and sodium bicarbonate. The tablets prepared according to these examples were subjected to in vitro dissolution in 500 ml of 0.01 N HCl using USP II (Paddle) apparatus at 50 rotations per minute. Table 9 provides the distribution of millimoles of alkalizer present in sustained release form and immediate release form along with in vitro release of tapentadol hydrochloride from a single tablet.

TABLE 9

Effect of sustained release form of alkalizer on release of drug from single unit dosage form

| Location in dosage form | Alkalizer in millimoles | Comparative Example 2 | Example 4 |
|---|---|---|---|
| Outer portion | Sustained release alkalizer | — | 2.5 |
|  | Immediate release alkalizer | 3.8 | 1.3 |
| Inner portion | Immediate release alkalizer | 0.2 | 0.2 |

TABLE 9-continued

Effect of sustained release form of alkalizer on release of drug from single unit dosage form

| In vitro release | | |
|---|---|---|
| Time in minutes | % Tapentadol released | |
| 5 | 44 | 67 |
| 10 | 46 | 75 |
| 15 | 46 | 80 |
| 30 | 48 | 85 |
| 60 | 50 | 86 |

From the above in vitro dissolution results, it is apparent that when the tablet of Comparative Example 2 included only immediate release form of alkalizer and did not have sustained release form of alkalizer, the release of the drug was incomplete (only 50% was released at the end of 60 minutes). Tablet of Example 4 had same amount of total alkalizer but the total alkalizer was divided in varying amounts of sustained release form of alkalizer and immediate release form of alkalizer. The in vitro dissolution data showed satisfactory release of 86% of tapentadol released in 60 minutes.

Example 6

The tablet composition of Example 6 represents compositions with alkalizer in both immediate release form and sustained release form. The total amount of alkalizers present in tablet composition of Example 6 was in amount of about 5.7 millimoles per tablet.

TABLE 10

Composition details of Example 6

| Category of ingredients | Ingredients | Example 6 Amount in mg (millimoles) | |
|---|---|---|---|
| Inner portion | | | |
| Drug | Model candidate drug susceptible to abuse (Hydrocodone Bitartrate) | 10 | |
| pH dependent polymer soluble in acidic medium | Methyl Methacrylate & Diethylaminoethyl Methacrylate Copolymer | 100 | |
| Excipient | Polyvinyl alcohol | 12.5 | |
| Alkalizer in immediate release form | Magnesium Oxide | 5.00 (0.124 millimoles) | |
|  | Sodium Carbonate | 10.80 (0.102 millimoles) | |
| Excipient | Tartaric Acid | 3 | |
|  | Butylated hydroxyanisole | 0.165 | |
| Outer portion | | | |
| Other drug not susceptible to abuse | Acetaminophen granule* in the form of directly compressed granules | 361.125 | |
| Alkalizer In Immediate Release And Sustained Release Form | Sodium Bicarbonate immediate release form | 85 (1.01 millimoles) | |
|  | Sodium Carbonate immediate release form | 25 (0.24 millimoles) | |
|  | Sustained Release Magnesium Oxide** | Magnesium Oxide | 218.00** 171 (4.24 millimoles) |
|  | | Ethyl cellulose | 40 |
|  | | Silicon dioxide | 7 |
| Excipients | Silicified Microcrystalline cellulose | 143.410 | |
|  | Crospovidone | 90 | |
|  | Colloidal silicon dioxide | 10 | |
|  | Talc | 7 | |
|  | Magnesium Stearate | 7 | |

The tablet composition of example 4 was prepared as per the procedure described in example 1. The tablet of Example 6 included about 5.7 millimoles of alkalizer which are magnesium oxide, sodium carbonate and sodium bicarbonate. The tablets prepared according to this example was subjected to in vitro dissolution in 500 ml of 0.01 N HCl using USP II (Paddle) apparatus at 50 rotations per minute. Table 11 provides the distribution of millimoles of alkalizer present in sustained release form and immediate release form along with in vitro release of hydrocodone from a single tablet.

TABLE 11

Effect of sustained release form of alkalizer on release of drug from single unit dosage form

| Location in dosage form | Alkalizer in millimoles | Example 6 |
|---|---|---|
| Outer portion | Sustained release alkalizer | 4.24 |
|  | Immediate release alkalizer | 1.25 |
| Inner portion | Immediate release alkalizer | 0.23 |

In vitro release

| Time in minutes | % Hydrocodone released |
|---|---|
| 5 | 68 |
| 10 | 79 |
| 15 | 83 |
| 30 | 86 |
| 60 | 87 |

The in vitro dissolution data showed satisfactory release of 87% of hydrocodone released in 60 minutes.

The invention claimed is:

1. An abuse deterrent oral solid dosage form comprising:
   an inner portion comprising a drug susceptible to abuse, a first immediate release form of one or more alkalizers and a pH dependent polymer soluble in acidic medium, and
   an outer portion, wherein the outer portion is devoid of drug susceptible to abuse and comprises a mixture of:
   a second immediate release form of one or more alkalizers; and
   a sustained release form of an alkalizer, the sustained release form comprising an alkalizer and a rate controlling excipient.

2. The abuse deterrent oral solid dosage form as claimed in claim 1, wherein the alkalizer of the sustained release form is released gradually in a sustained manner over a period of about 2 hours in 0.01 N hydrochloric acid.

3. The abuse deterrent oral solid dosage form of claim 1, wherein the one or more alkalizers in the second immediate release form is sodium carbonate, sodium bicarbonate, magnesium oxide or any mixture thereof, and the alkalizer in the sustained release form is magnesium oxide.

4. The abuse deterrent oral solid dosage form of claim 1, wherein the pH dependent polymer soluble in acidic medium is methyl methacrylate and diethylaminoethyl methacrylate copolymer.

5. The abuse deterrent oral solid dosage form of claim 1, wherein the amount of the alkalizer in the immediate release forms is in the range of about 0.2 to 2.8 millimoles and the amount of the alkalizer in the sustained release form is in the range of about 1.4 to 6 millimoles.

6. The abuse deterrent oral solid dosage form of claim 1, wherein the weight ratio of (i) the total amount of alkalizers and (ii) the pH dependent polymer soluble in acidic medium is the range of 2.0 to 3.0.

7. The abuse deterrent oral solid pharmaceutical composition of claim 1, wherein the rate controlling excipient is selected from ethyl cellulose, cellulose acetate, hydroxyethyl cellulose, hydroxypropyl methyl cellulose, methyl cellulose, carboxymethyl cellulose, hydroxyethyl methylcellulose, hydroxypropyl cellulose, fatty acids, lower alcohol fatty acid ester, glycerol fatty acid esters, acetylated glycerol fatty acid esters, lactic acid derivatives of mono/diglycerides, sorbitan fatty acid esters, reaction mixtures of polyols and fatty acids, glycerides, vegetable oils, hydrogenated vegetable oils, sterols, and mixtures thereof.

8. The abuse deterrent oral solid pharmaceutical composition of claim 1, wherein the rate controlling excipient is selected from ethyl cellulose, cellulose acetate, hydroxyethyl cellulose, hydroxypropyl methyl cellulose, methyl cellulose, carboxymethyl cellulose, hydroxyethyl methylcellulose, and hydroxypropyl cellulose.

9. The abuse deterrent oral solid pharmaceutical composition of claim 1, wherein the rate controlling excipient is ethyl cellulose.

10. The abuse deterrent oral solid pharmaceutical composition of claim 1, wherein the sustained release form is in the form of an admixture, granules, extrudates or coated particles.

11. The abuse deterrent oral solid dosage form of claim 1, wherein the amount of the alkalizer in the immediate release form is in the range of about 0.2 to 2.8 millimoles and the amount of the alkalizer in the sustained release form is in the range of about 1.4 to 4.2 millimoles and the total amount of alkalizer is in the range of about 3.75 to 6 millimoles per unit abuse deterrent oral solid dosage form.

12. The abuse deterrent oral solid dosage form of claim 1, wherein the total amount of alkalizer is in the range of about 3.75 to 6 millimoles per unit abuse deterrent oral solid dosage form.

13. A method of treating a patient having hyperacidity with a drug susceptible to abuse, the method comprising administering an abuse deterrent oral solid dosage form according to claim 1 to the patient.

14. The method of claim 13, wherein the abuse deterrent oral solid dosage form is administered to the patient in the fed state.

15. A method of treating a patient having acid rebound effect with a drug susceptible to abuse, the method comprising administering an abuse deterrent oral solid dosage form according to claim 1 to the patient.

16. The method of claim 15, wherein the abuse deterrent oral solid dosage form is administered to the patient in the fed state.

* * * * *